US00PP32017P2

(12) United States Plant Patent
Nelson et al.

(10) Patent No.: US PP32,017 P2
(45) Date of Patent: Jul. 28, 2020

(54) STRAWBERRY PLANT NAMED 'BG-9.3147'

(50) Latin Name: *Fragaria ananassa*
Varietal Denomination: BG-9.3147

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: BERRY GENETICS, INC., Freedom, CA (US)

( * ) Notice: Subject to any disclaimer, the term of this patent is extended or adjusted under 35 U.S.C. 154(b) by 0 days.

(21) Appl. No.: 16/602,399

(22) Filed: Sep. 30, 2019

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Foley & Lardner LLP

(57) ABSTRACT

This invention relates to a new and distinct variety of strawberry plant named 'BG-9.3147'. This new strawberry plant named 'BG-9.3147' is primarily adapted to the growing conditions of the central coast of California, and is primarily characterized by its achenes typically set below the surface of the fruit, very good fruit flavor with firm flesh, moderately creased fruit, early time of first flower and fruit, medium plant size with medium yellow green foliage; and strongly pubescent fruiting trusses with hairs typically positioned strongly outward.

4 Drawing Sheets

Latin name of the genus and species of the plant claimed: *Fragaria ananassa.*

Variety denomination: 'BG-9.3147'.

BACKGROUND OF THE INVENTION

The present invention relates to a new and distinct strawberry variety named 'BG-9.3147'. This new variety is a result of a controlled cross made in 2009 in an ongoing breeding program between strawberry variety designated 'Ventana' (U.S. Plant Pat. No. 14,203) as the seed (female) parent, and strawberry variety designated 'BG-1975' (U.S. Plant Pat. No. 17,725) as the pollen (male) parent. The variety is botanically known as *Fragaria ananassa.*

The seedling resulting from the aforementioned cross was selected from a controlled breeding plot in Ventura County, Calif. in the winter of 2011. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-9.3147' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-9.3147', which in combination distinguish this strawberry plant as a new and distinct variety:

1. Achenes typically set below the surface of the fruit;
2. Very good fruit flavor with firm flesh;
3. Moderately creased fruit;
4. Early time of first flower and fruit;
5. Medium plant size with medium yellow green foliage; and
6. Strongly pubescent fruiting trusses with hairs typically positioned strongly outward.

The strawberry variety that is believed to be most closely related to the new variety 'BG-9.3147' is 'BG-3.324' (U.S. Plant Pat. No. 23,256). In side-by-side comparisons to the similar strawberry variety 'BG-3.324', 'BG-9.3147' differs by the following combination of characteristics as described in Table 1.

TABLE 1

| Characteristic | 'BG-9.3147' | 'BG-3.324' (U.S. Plant Pat. No. 23,256) |
|---|---|---|
| Fruit: marketable yield (gm/pit) | 1,122 | 1,049 |
| Fruit: season average size (gm) | 28.2 | 29.1 |
| Fruit: flavor | Very good | Good |
| Terminal leaf: serrations per leaf | 19.5 | 16.8 |
| Foliage: color of upper surface | Medium yellow green | Ranges from light to medium yellow green |
| Fruiting truss: anthocyanin intensity | Weak | Medium |
| Fruiting truss: pubescence | Strong | Medium |
| Disease reactions: Fusarium wilt | Moderately resistant | Susceptible |

For identification, a series of molecular markers have been determined for this new variety.

'BG-9.3147' differs from its parents, 'Ventana' and 'BG-1975' by the following combination of characteristics as described in Tables 2 and 3.

TABLE 2

| Characteristic | 'BG-9.3147' | 'Ventana' (U.S. Plant Pat No. 14,203) |
|---|---|---|
| Fruit: size | Large | Medium |
| Fruit: marketable yield | Ranges from medium to high | Medium |
| Plant: vigor | Medium | Ranges from medium to large |
| Fruit: flavor | Very good | Fair |

TABLE 3

| Characteristic | 'BG-9.3147' | 'BG-1975' (U.S. Plant Pat. No. 17,725) |
|---|---|---|
| Fruit: size | Large | Medium |
| Fruit: marketable yield | Ranges from medium to high | Medium |
| Disease reactions: Fusarium wilt | Moderately resistant | Susceptible |
| Fruit: evenness of surface | Ranges from slightly to strongly uneven | Slightly uneven |

BRIEF DESCRIPTIONS OF THE PHOTOGRAPHS

The accompanying color photographs illustrate the overall appearance of typical specimens of the new strawberry variety 'BG-9.3147' at various stages of development, as true as it is reasonably possible with color reproductions of this type. Color in the photographs may differ slightly from the color value cited in the botanical descriptions which accurately describe the color of 'BG-9.3147'. The depicted plant and plant parts of the new strawberry variety 'BG-9.3147' are approximately six months old. The photographs were taken in Ventura County, Calif.

DETAILED BOTANICAL DESCRIPTION

Figure 1:
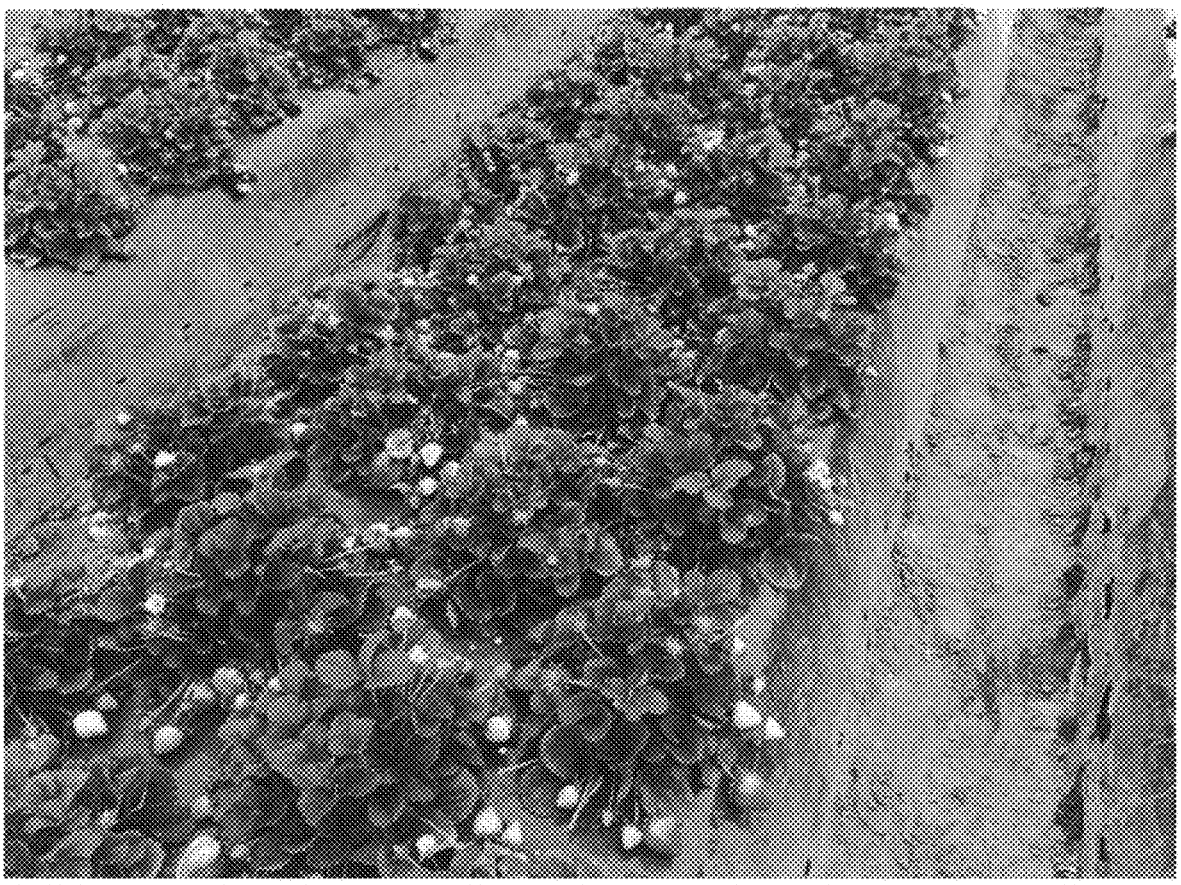
FIG. 1 shows typical fruiting field characteristics of 'BG-9.3147', taken in the month of March 2019.
Figure 2:
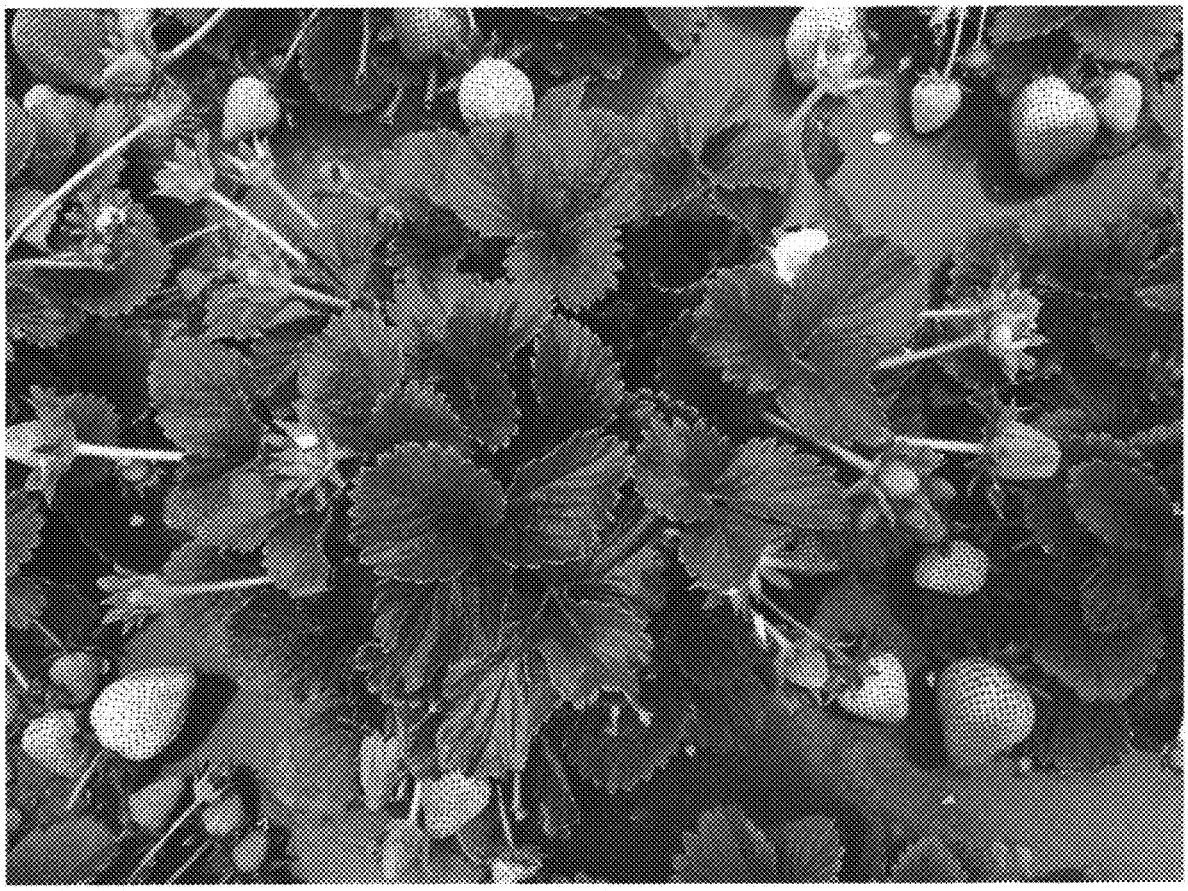
FIG. 2 shows a close-up view of a typical plant of 'BG-9.3147', taken in the month of March 2019.
Figure 3:
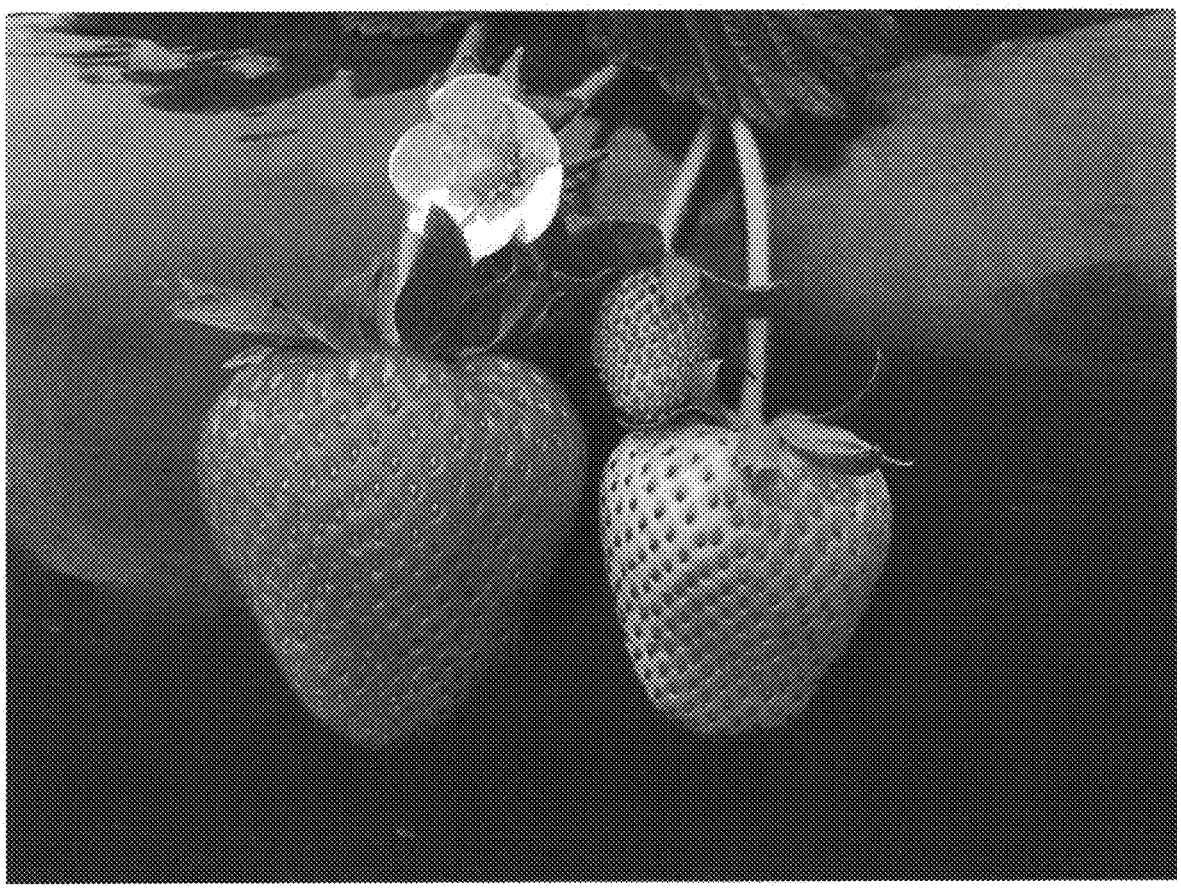
FIG. 3 shows typical mature and immature field fruit of 'BG-9.3147', taken in the month of March 2019.
Figure 4:
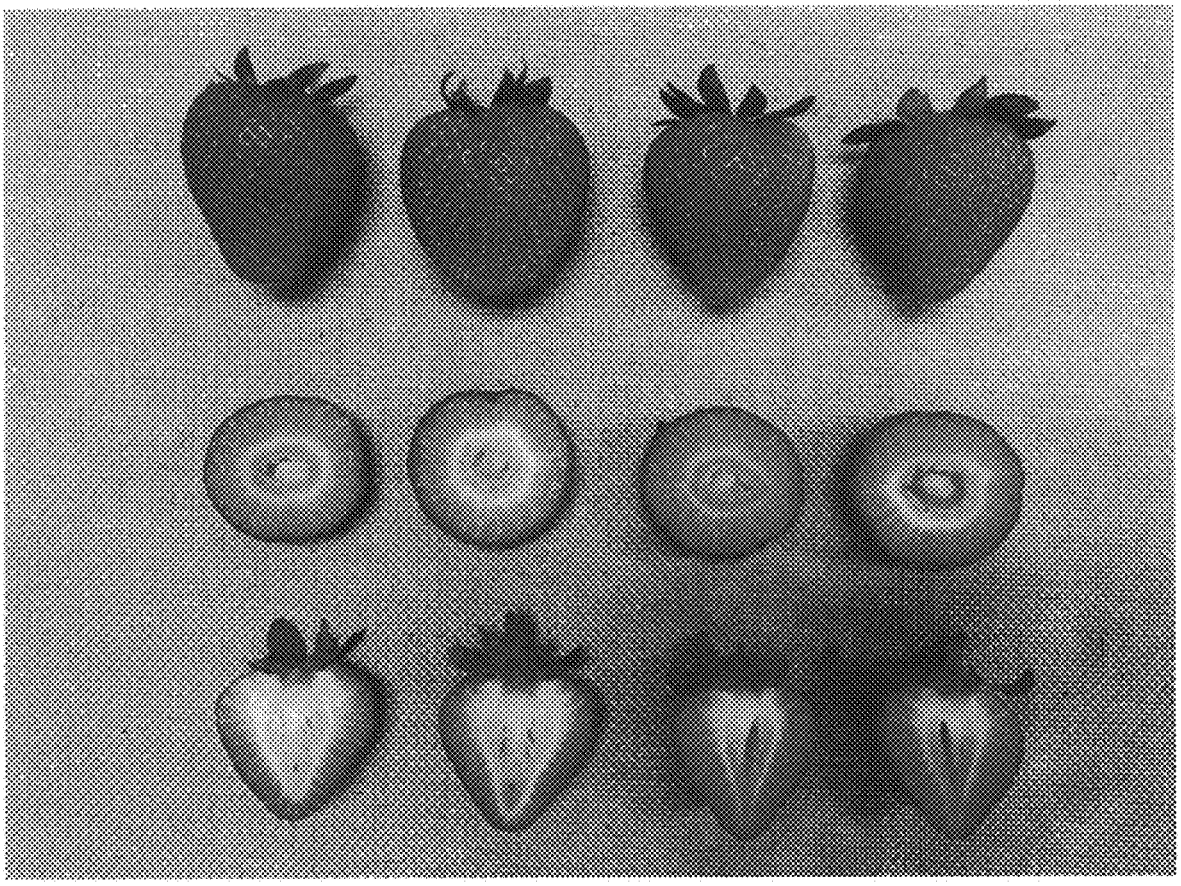
FIG. 4 shows typical internal and external mature fruit characteristics of 'BG-9.3147', taken in the month of March 2019.

The new variety 'BG-9.3147' has not been observed under all possible environmental conditions. The characteristics of the new variety 'BG-9.3147' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-9.3147', unless otherwise noted, are based on observations taken during the 2019 growing season in Ventura County, Calif. These measurements and ratings were taken from plants of 'BG-9.3147' dug from a high-elevation nursery located in Siskiyou County, Calif. during early October 2018 and planted approximately four to five days later in Ventura County, Calif. The approximate age of the observed plants is six months. Yield observations including average weight and marketable yield, along with fruit quality characteristics including soluble solids, are averaged from five years of data collected from the 2014 through 2018 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'BG-9.3147'.

Fruit characteristics:

*Color of mature fruit*.—RHS 46A (red).

*Color of internal flesh* (*excluding core*).—RHS 45C (medium red).

*Color of core*.—RHS 38B (medium red).

*Average length* (*cm*).—4.2.

*Average width* (*cm*).—3.9.

*Size*.—Large.

*Average length/width ratio*.—1.08 (ranges from as long as broad to slightly longer than broad).

*Average calyx diameter* (*cm*).—4.6.

*Season average weight* (*gm*).—28.2.

*Achene color, shaded side*.—RHS 153C (yellow green group).

*Achene color, sun-exposed side*.—RHS 185A (greyed purple group).

*Average achene weight* (*mg*).—0.42.

*Average achenes per berry*.—400.

*Season marketable yield* (*gm/plant*).—1,122.

*Predominant shape*.—Cordate (cordiform).

*Difference in shape between primary and secondary fruit*.—Ranges from moderate to large.

*Band without achenes*.—Narrow.

*Evenness of surface*.—Ranges from slightly uneven to strongly uneven.

*Evenness of color*.—Even or very slightly uneven.

*Glossiness*.—Ranges from medium to strong.

*Insertion of achenes*.—Below surface.

*Position of calyx attachment*.—Inserted.

*Attitude of sepals*.—Outward.

*Size of calyx in relation to fruit diameter*.—Slightly larger.

*Adherence of calyx* (*when fully ripe*).—Strong.

*Firmness of flesh*.—Firm.

*Distribution of red color of the flesh*.—Marginal and central.

*Hollow center expression*.—Moderate.

*Flavor*.—Very good.

*Soluble solids* (% *brix*).—7.5.

*Time of first flowering*.—Early (late November in Ventura County, Calif.).

*Time of first fruit*.—Early (late December in Ventura County, Calif.).
*Harvest period*.—Late December to May (in Ventura County, Calif.).
*Harvest maturity*.—Early season (March).
*Type of bearing*.—Not remontant.

Plant characteristics:
*Average height* (*cm*).—20.0.
*Average spread* (*cm*).—33.7.
*Size*.—Medium.
*Habit*.—Upright.
*Density*.—Medium.
*Vigor*.—Medium.

Stolon characteristics:
*Color*.—RHS 146D (yellow green group).
*Anthocyanin coloration*.—RHS 182C (greyed red group).
*Anthocyanin intensity*.—Ranges from weak to medium.
*Pubescence*.—Dense.
*Attitude of hairs*.—Slightly outward.
*Average quantity in nursery* (*per square foot*).—5 to 6 (medium).
*Average diameter at the bract* (*mm*).—3.1 (medium).

Terminal leaflet characteristics:
*Average length* (*cm*).—5.6.
*Average width* (*cm*).—5.3.
*Average area terminal* ($cm^2$).—29.6.
*Average length/width ratio*.—1.04 (longer than broad).
*Shape of base*.—Obtuse.
*Margins* (*shape of teeth*).—Obtuse (serrate to crenate).
*Average serrations per leaf*.—19.5.

Foliage characteristics:
*Color of upper surface*.—RHS 146A (medium yellow green).
*Color of underside*.—RHS 147C (yellow green group).
*Number of leaflets*.—3.
*Leaf size*.—Ranges from medium to small.
*Average length* (*cm*).—8.2.
*Average width* (*cm*).—11.3.
*Average area foliage* ($cm^2$).—92.6.
*Shape in cross section*.—Slightly concave.
*Interveinal blistering*.—Ranges from medium to strong.
*Leaf glossiness*.—Ranges from medium to strong.
*Leaf variegation*.—Absent.

Petiole characteristics:
*Petiole color*.—RHS 144B (yellow green group).
*Average length* (*cm*).—12.1.
*Average diameter* (*mm*).—2.8.
*Petiolule color*.—RHS 144B (yellow green group).
*Petiolule average length* (*mm*).—4.6.
*Attitude of hairs*.—Strongly outward.
*Frequency of bract leaflets*.—Ranges from few to none (0% occurrence).
*Size of bract leaflets*.—N/A.
*Pubescence*.—Ranges from heavy to moderate.

Stipule characteristics:
*Color*.—RHS 145D (yellow green group).
*Anthocyanin coloration*.—RHS 55B (red group).
*Anthocyanin intensity*.—Weak.
*Average length* (*mm*).—12.8.
*Average width* (*mm*).—10.0.

Fruiting truss characteristics:
*Anthocyanin coloration*.—RHS N170C (greyed orange group).
*Anthocyanin intensity*.—Weak.
*Average length at maturity* (*cm*).—21.6.
*Position relative to foliage*.—Ranges from level with to above.
*Flower quantity* (*average per plant season long*).—50 to 60 (medium).
*Pedicel attitude of hairs*.—Strongly outward.
*Pubescence*.—Strong.
*Attitude at first pick*.—Prostrate.

Flower characteristics:
*Petal color*.—RHS NN155C (white group).
*Sepal color*.—RHS 137A (green group).
*Corolla* (*flower*) *average diameter* (*mm*).—28.8 (ranges from medium to large).
*Calyx average diameter* (*mm*).—39.2.
*Petal average length* (*mm*).—11.1.
*Petal average width* (*mm*).—11.4.
*Petal average length/width ratio*.—0.97 (as long as broad).
*Average petals per flower*.—6.9.
*Sepal average length* (*mm*).—15.1.
*Sepal average width* (*mm*).—5.7.
*Sepal average length/width ratio*.—2.65.
*Average sepals per flower*.—14.6.
*Size of calyx relative to corolla*.—Larger.
*Size of inner calyx relative to outer calyx*.—Same.
*Relative position of petals* (*flowers with* 5 *or* 6 *petals*).—Overlapping.

Reproductive organs:
*Receptacle color*.—RHS 147C (yellow green group).
*Pollen color*.—RHS 14A (yellow orange group).
*Stamen*.—Present.
*Pollen amount*.—Abundant.

Disease and pest reactions:
*Powdery mildew* (*sphaerotheca macularis*).—Moderate.
*Angular leaf spot* (*xanthomonas fragariae*).—Susceptible.
*Botrytis fruit rot* (*botrytis cinerea*).—Moderately susceptible.
*Fusarium wilt* (*fusarium oxysporum*).—Moderately resistant.
*Anthracnose crown rot* (*colletotrichum fragariae*).—Susceptible.
*Two-spotted spider mite* (*tetranychus urticae*).—Moderately susceptible.

We claim:

1. A new and distinct strawberry plant named 'BG-9.3147', as herein described and illustrated.

* * * * *